US012626790B2

(12) United States Patent
Delgrande et al.

(10) Patent No.: US 12,626,790 B2
(45) Date of Patent: May 12, 2026

(54) POINT-OF-CARE TESTING (POCT) INSTRUMENT AND POCT SYSTEM

(71) Applicant: Roche Diagnostics Operations, Inc., Indianapolis, IN (US)

(72) Inventors: Diego Delgrande, Lucerne (CH); Ulrich Porsch, Weinheim (DE); Nina Suter, Bear (CH); Mathias Wilhelms, Schwetzingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1194 days.

(21) Appl. No.: 17/205,395

(22) Filed: Mar. 18, 2021

(65) Prior Publication Data
US 2021/0295959 A1     Sep. 23, 2021

(30) Foreign Application Priority Data
Mar. 23, 2020     (EP) .................................... 20164926

(51) Int. Cl.
| | |
|---|---|
| *G16H 10/40* | (2018.01) |
| *G06F 1/26* | (2006.01) |
| *G06F 21/31* | (2013.01) |
| *G16H 40/63* | (2018.01) |

(52) U.S. Cl.
CPC ............. *G16H 10/40* (2018.01); *G06F 1/263* (2013.01); *G06F 21/31* (2013.01); *G16H 40/63* (2018.01)

(58) Field of Classification Search
CPC ......... G16H 10/40; G16H 40/63; G06F 1/263
See application file for complete search history.

(56) References Cited

U.S. PATENT DOCUMENTS

| | | | |
|---|---|---|---|
| 5,961,804 A | 10/1999 | Jacobson et al. | |
| 7,591,801 B2 * | 9/2009 | Brauker ................. | G16H 20/17 |
| | | | 604/161 |
| 8,760,363 B2 | 6/2014 | Lin et al. | |
| 9,858,520 B2 | 1/2018 | Holostov et al. | |
| 2008/0220814 A1 | 9/2008 | Hedtke et al. | |

(Continued)

FOREIGN PATENT DOCUMENTS

| | | |
|---|---|---|
| EP | 2541370 A1 | 1/2013 |
| EP | 3091460 A1 | 11/2016 |
| EP | 2859427 B1 | 8/2019 |

(Continued)

OTHER PUBLICATIONS

Dionysios C. Christodouleas, Balwinder Kaur, and Parthena Chorti, "From Point-of-Care Testing to eHealth Diagnostic Devices (eDiagnostics)", ACS Central Science 2018 4 (12), 1600-1616 (Year: 2018).*

(Continued)

*Primary Examiner* — Larry D Riggs, II
*Assistant Examiner* — Emilie A Smith
(74) *Attorney, Agent, or Firm* — Bose McKinney & Evans LLP

(57) ABSTRACT

A point of care testing (POCT) instrument for analyzing biological samples and a POCT system comprising a plurality of such POCT instruments is proposed. The POCT instrument comprises a housing, a measurement unit designed for collecting data indicative of at least one biological parameter of a biological sample, a main display, and an auxiliary display.

26 Claims, 8 Drawing Sheets

(56) References Cited

U.S. PATENT DOCUMENTS

| | | |
|---|---|---|
| 2013/0169512 A1 | 7/2013 | Yang |
| 2016/0224302 A1 | 8/2016 | Imana |

FOREIGN PATENT DOCUMENTS

| | | |
|---|---|---|
| JP | H08-47485 A | 2/1996 |
| JP | 2009-040731 A | 2/2009 |
| JP | 2009-265260 A | 11/2009 |
| JP | 2013-099499 A | 5/2013 |
| JP | 2015-165365 A | 9/2015 |
| WO | 2012/044201 A2 | 4/2012 |
| WO | 2016/107308 A1 | 7/2016 |
| WO | 2019/138681 A1 | 7/2019 |

OTHER PUBLICATIONS

Image Quality Characteristics of Handheld Display Devices for Medical Imaging Yamazaki A, Liu P, Cheng WC, Badano A (2013) Image Quality Characteristics of Handheld Display Devices for Medical Imaging. PLOS ONE 8(11): e79243. (Year: 2013).*
P. Neuzil, C. D. M. Campos, C. C. Wong, J. B. W. Soon, J. Reboud, and A. Manz; "From chip-in-a-lab to lab-on-a-chip: towards a single handheld electronic system for multiple application-specific lab-on-a-chip (ASLOC)"; Lab Chip, 2014, 14, 2168-2176. (Year: 2014).*

\* cited by examiner

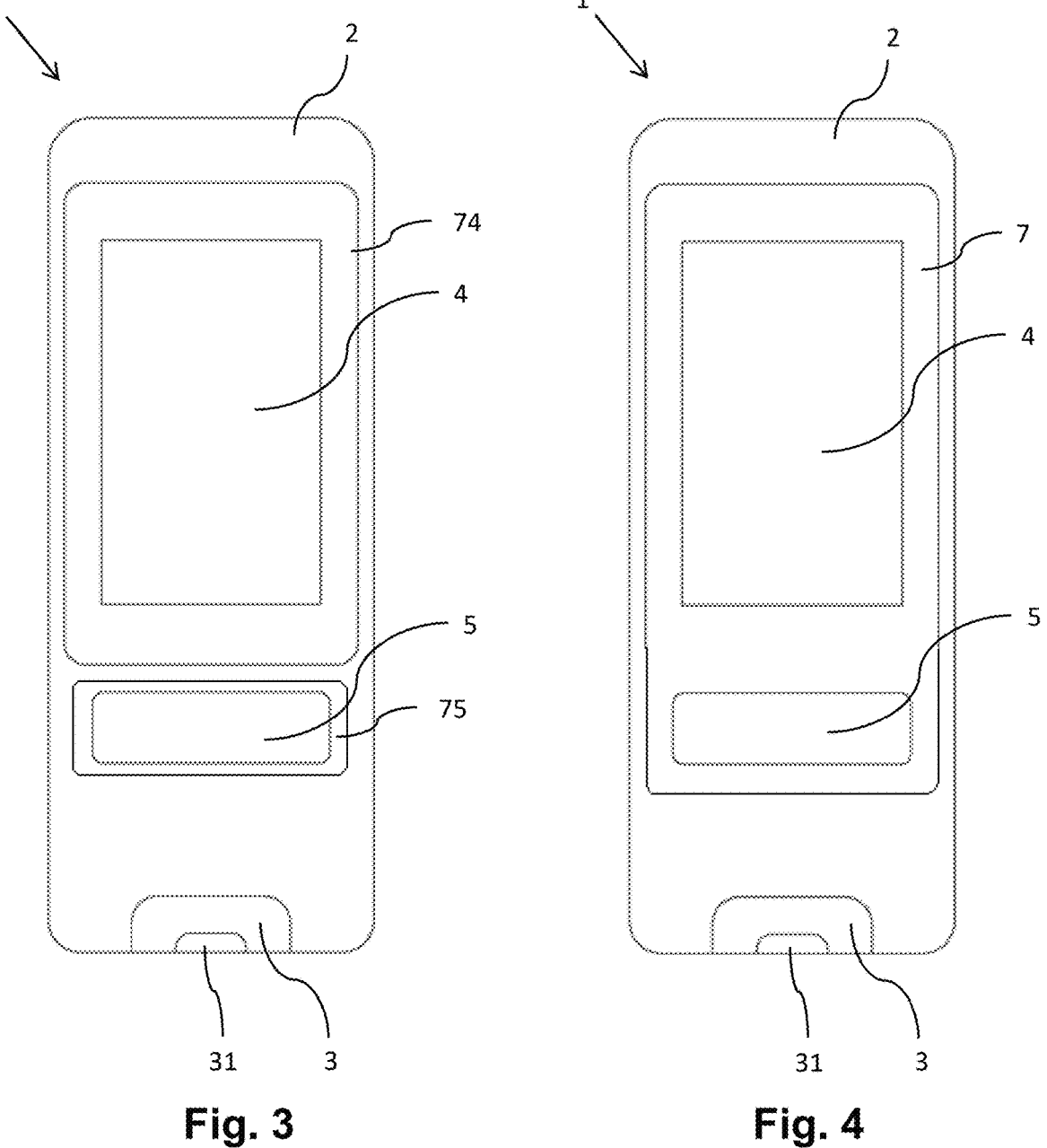
Fig. 3                    Fig. 4

1

POINT-OF-CARE TESTING (POCT) INSTRUMENT AND POCT SYSTEM

CROSS-REFERENCE TO RELATED APPLICATIONS

This application claims priority to EP 20164926.6, filed Mar. 23, 2020, which is hereby incorporated by reference.

BACKGROUND

The present disclosure generally relates to a point of care testing (hereinafter referred to as "POCT") instrument and a POCT system comprising such POCT instruments.

POCT has a major effect on medical decisions as it allows providing physicians with decisive information and thus plays a vital role in public health care. POCT is performed mainly by nurses or medical staff trained for operating the POCT instruments available at the site of patient care, such as hospitals, emergency departments, intensive care units, primary care setting, medical centers, patient homes, a physician's office, a pharmacy, or a site of an emergency.

POCT systems at a site often comprises a large number of POCT instruments and, in many cases, the staff applies sticky labels on the POCT instruments for organizational purposes, such as e.g., indicating a staff member or a unit to which the respective POCT instrument is allocated.

However, sticky labels are considered hygienically problematic, since, in practice, it can be difficult to avoid accumulation of dirt on the sticky label, in particular, at edges and/or on the adhesive side of the sticky label if it partly detaches. The dirt can possibly lead to cross-contamination that could endanger personal and patients, in particular, since many sites in which POCT instruments are used are especially exposed to pathogens such as e.g., multi-resistant germs.

Therefore, there is a need for providing POCT instruments that in practice can be kept hygienic with reasonable effort.

SUMMARY

According to the present disclosure, a point of care testing (POCT) instrument for analyzing biological samples is presented. The POCT instrument can comprise a housing, a measurement unit designed for collecting data indicative of at least one biological parameter of a biological sample, a main display, and an auxiliary display.

Accordingly, it is a feature of the embodiments of the present disclosure to provide POCT instruments that in practice can be kept hygienic with reasonable effort. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 3 illustrates a front view of a POCT instrument in form of a portable device according to an embodiment of the present disclosure.

FIG. 4 illustrates a front view of another POCT instrument in form of a portable device according to an embodiment of the present disclosure.

DETAILED DESCRIPTION

Figure 1:
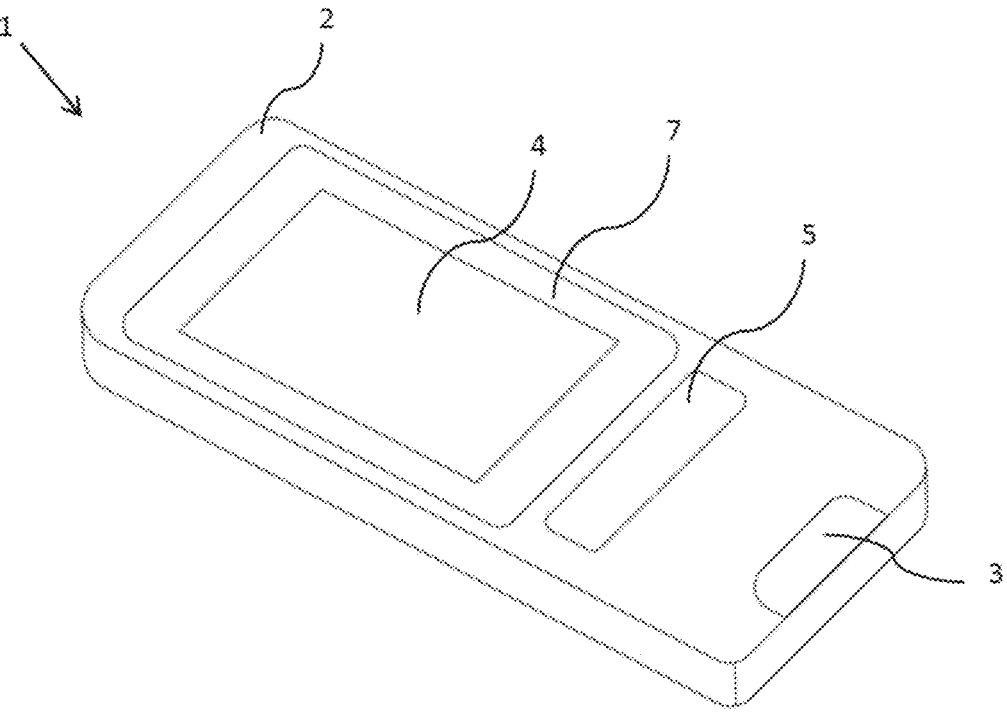
FIG. 1 illustrates a perspective view on a POCT instrument in form of a portable device according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A point of care testing (POCT) instrument for analyzing biological samples is proposed. The POCT instrument can comprise a housing, a measurement unit designed for collecting data indicative of at least one biological parameter of a biological sample, a main display, and an auxiliary display.

According to some embodiments, the main display can be constructed based on a first display technology and the auxiliary display can be constructed based on a second display technology. According to some specific embodiments, the second display technology can consume less power than the first display technology, e.g., less than half the power per time unit per area.

According to some embodiments, the auxiliary display can be designed for displaying content without power consumption.

According to some embodiments, the auxiliary display can be designed for displaying a constant content.

According to some embodiments, the main display can be larger than the auxiliary display, e.g., the visible area of the display can be at least three times larger than that of the auxiliary display.

According to some embodiments, the main display can comprise a touch functionality and the auxiliary display may not comprise a touch functionality.

According to some embodiments, the main display and the auxiliary display can be each integrated into the housing such that content displayed on each of the main display and the auxiliary display can be visible from outside the housing.

According to some embodiments, the main display respectively, i.e., and/or, a transparent protective layer arranged on top of the main display can be arranged in a flush manner with a side of the housing and the auxiliary display respectively, i.e., and/or, a transparent protective layer arranged on top of the auxiliary display can be arranged in a flush manner with the same side of the housing.

According to some embodiments, the main display can be arranged on a first side of the housing and the auxiliary display can be arranged on a second side of the housing. The first side and the second side can be different.

According to some embodiments, the main display respectively, i.e., and/or, a transparent protective layer arranged on top of the main display can be arranged in a flush manner with a first side of the housing and the auxiliary display respectively, i.e., and/or, a transparent protective layer arranged on top of the auxiliary display can be arranged in a flush manner with a second side of the housing. The first side and the second side can be different.

According to some embodiments, the main display and the auxiliary display can be arranged under a common transparent protective layer.

According to some embodiments, the main display and the auxiliary display can be arranged on a same side of the housing and may not be overlapping.

According to some embodiments, the POCT instrument can comprise a control unit that can be designed for controlling the content displayed on the auxiliary display.

According to some embodiments, the POCT instrument can comprise a switch unit designed for shutting off the main display but not the auxiliary display.

According to some embodiments, the average number of pixels per area-unit of the main display can be at least four times larger than that of the auxiliary display.

According to some embodiments, the housing can comprise no openings or only openings for the measurement unit.

According to some embodiments, circuitry of the auxiliary display can be independent of circuitry of the main display.

According to some embodiments, the POCT instrument can comprise a first power source and a second power source. The POCT instrument can be designed such that the main display can be supplied by the first power source and the auxiliary display can be supplied by the second power source.

According to some embodiments, the auxiliary display can require power for changing displayed content. The POCT instrument can be designed so that the command for changing content displayed on the auxiliary display and the necessary energy for this changing can be induced from an external source.

According to some embodiments, the POCT instrument can be designed for changing content displayed on the auxiliary display according to instructions inputted via an external input device.

According to some embodiments, the POCT instrument can comprise an authorization module for selectively authorizing a user of the POCT instrument to use certain functionality of the POCT instrument.

Further, a POCT system is proposed. The POCT system can comprise a plurality of POCT instruments and a system control unit. The system control unit can be designed for changing the content displayed on the auxiliary displays of the POCT instruments.

According to some embodiments, the POCT system can be designed for automatically adjusting the content displayed on the auxiliary display of a POCT instrument of the plurality of POCT instruments to data stored in the system control unit.

According to some embodiments, the POCT system can be designed such that content displayed on the auxiliary display of an POCT instrument of the plurality of POCT instruments can be based on data stored in the system control unit and, if this stored data is adjusted in the system control unit, the adjusted data can be automatically transmitted to the POCT instrument and content based on the adjusted data can be displayed on the auxiliary display.

According to some embodiments, the POCT instrument can be designed for transmitting information concerning test results to the system control unit.

Referring initially to FIG. 1, FIG. 1 illustrates an example of a proposed POCT instrument 1 in form of a portable (or handheld) device. The POCT instrument 1 can comprise a housing 2, a measurement unit 3, a main display 4, and an auxiliary display 5. The measurement unit 3, the main display 4 and the auxiliary display 5 can each be arranged in the housing 2. The main display 4 and the auxiliary display 5 can each be a visual display, i.e., can be designed for displaying visual content. The main display 4 and the auxiliary display 5 can each be integrated into the housing 2 such that content displayed on each of the main display 4 and the auxiliary display 5 can be visible from outside the housing 2.

Providing a POCT instrument 1 comprising an auxiliary display 5 for displaying information that otherwise would be attached using a sticky label can allow for decreasing the incentive for attaching hygienically problematic sticky labels to the POCT instrument 1, which in turn can allow for supporting the 'clean-ability' of the POCT instrument 1 and thereby can ease the effort for keeping the POCT instrument 1 hygienic.

The POCT instrument 1 can be designed for analyzing biological samples, e.g., in vitro and/or in vivo. The analyzed biological sample can e.g., comprise a body fluid (urine, blood, saliva, etc.) and/or be a body part. The measurement unit 3 can be designed for collecting data indicative of at least one biological parameter of such a biological sample. Such a biological parameter can e.g., concern coagulation, infectious disease, blood gas and electrolytes, blood glucose, hemoglobin, cholesterol, cardiac markers, pregnancy, fecal occult blood, urine, food pathogens, drug abuse, A1C, blood pressure, creatinine, liver function, heart rate, pulse parameters, and/or body temperature. The measurement unit 3 can comprise one or more sensors, e.g., cameras, temperature sensors, gyroscopes, accelerometers, and/or electrodes. The measurement unit 3 can e.g., be designed for collecting data of biological material provided on/in test strips, cartridges, disks, and/or buds.

Figure 5:
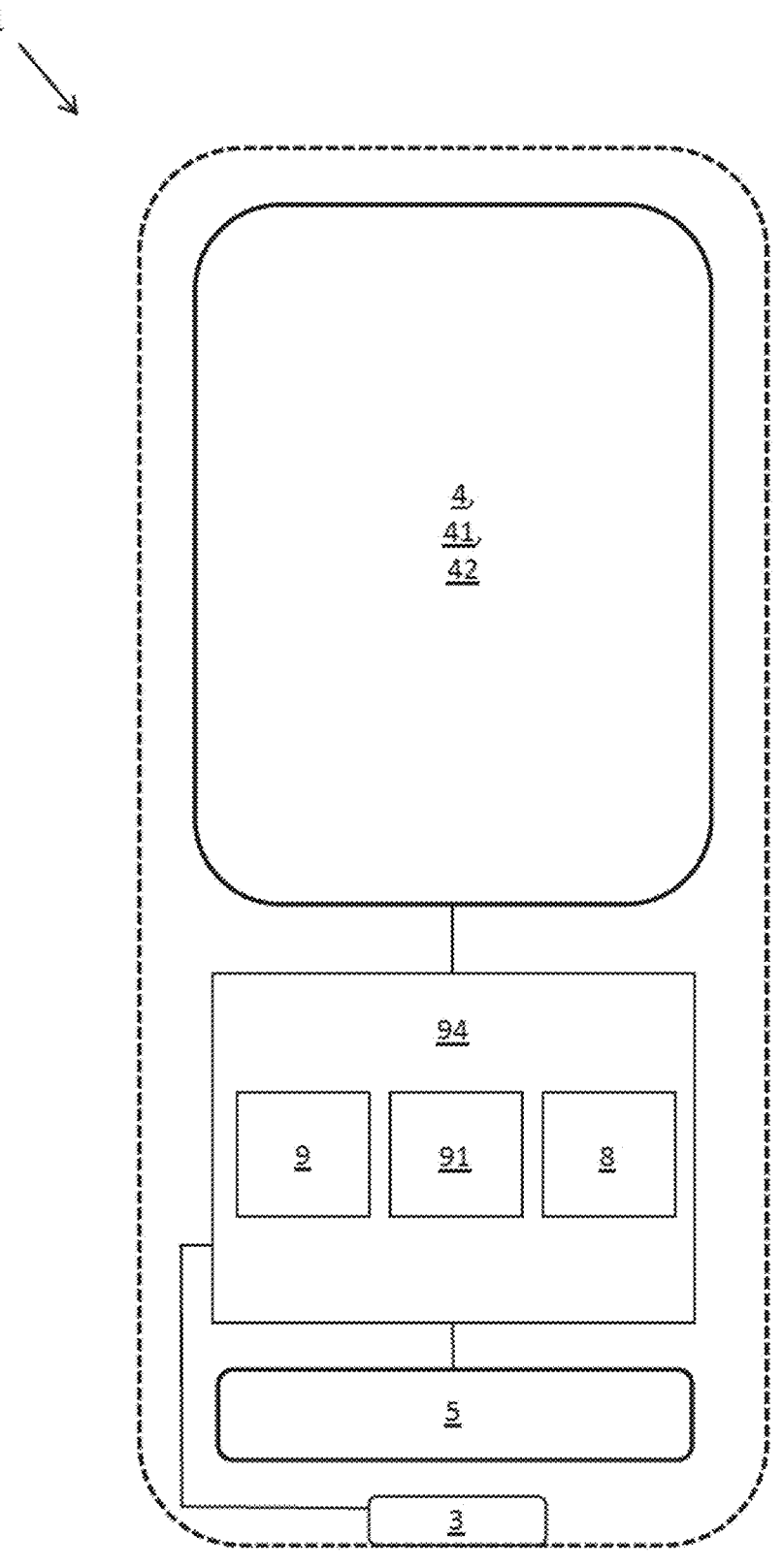
FIG. 5 illustrates a schematic of a POCT instrument's electronics according to an embodiment of the present disclosure.

The POCT instrument 1 can comprise an evaluation unit (that e.g., can be part of a control unit 9 as seen in FIG. 5) that can be configured for evaluating a quantitative and/or qualitative result in connection with the at least one biological parameter. According to some specific embodiments, the POCT instrument 1 is configured for displaying the result on the main display 4. In an example, the measurement unit 3 comprises a camera designed for taking a picture of a urine test strip; the evaluation unit is configured for evaluating a value concerning a glucose concentration based on the picture; and the main display 4 is configured for displaying the value to a user. In addition or alternatively, the measurement unit 3 can comprise electrodes for measuring the glucose concentration.

Figure 2:
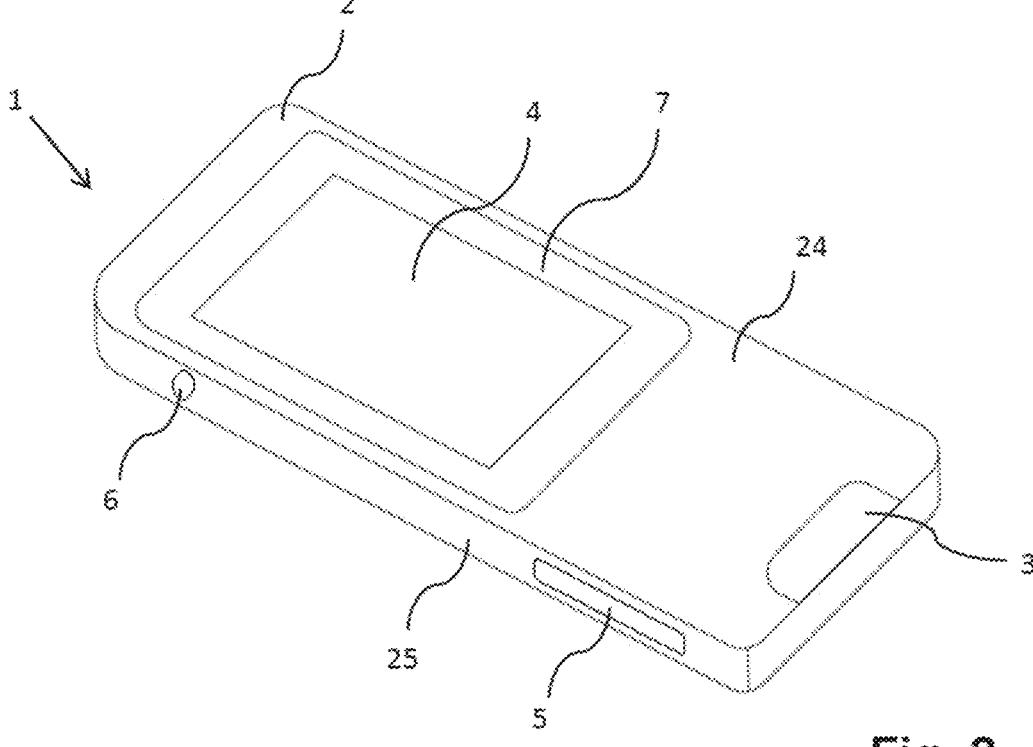
FIG. 2 illustrates a perspective view on another POCT instrument in form of a portable device according to an embodiment of the present disclosure.

The main display 4 and the auxiliary display 5 can each be arranged on a surface of the housing 2, such that the content displayed on the main display 4 and the auxiliary display 5 each can be visible from outside the housing 2. In the example of FIG. 1, the main display 4 and the auxiliary display 5 can each be arranged on a common side of the housing 2. However, they can as well be arranged on different sides of the housing's surface, such as shown in FIG. 2, wherein the main display 4 can be arranged on a first side 24 of the housing 2 and the auxiliary display 5 can be arranged on a second side 25 of the housing 2. Arranging the auxiliary display 5 on a different side than the main display 4 can increase the probability that the information displayed on the auxiliary display 5 can be directly visible when the POCT instrument 1 is put down and/or can increase the probability that at least one of that the two displays 4, 5 can be directly visible.

According to some embodiments, the POCT instrument 1 can be a handheld instrument that can be at least almost a flat cuboid, wherein the main display 4 can be arranged on a large side of the POCT instrument 1 and the auxiliary display 5 can be arranged on a small side of the POCT instrument 1. In an example, a POCT instrument 1 can be at least almost a flat cuboid in that the convex hull of the POCT instrument 1 can occupy more than about 90% of the volume of the smallest cuboid comprising the POCT instrument 1, wherein the smallest cuboid comprising the POCT instrument 1 can be defined by edges of lengths a, b, and c, wherein a can be shorter than b, e.g., less than half the length of b, and b can be shorter than c, e.g., each less than half the length of c, and a large side of the POCT instrument 1 can be a side associated with the edges b and c, and a small side can be a side associated with the edge a and b or a and c. Such an example is shown in FIG. 2. In practical use, such an instrument can be often put down on one of its large sides so that the small sides can remain visible, and arranging the auxiliary display 5 on such a small side can increase the probability that the auxiliary display 5 can be visible when the POCT instrument 1 is put down.

The main display 4 can be configured for displaying data needed for the normal operation of the POCT instrument 1, e.g., test results, test information, authorization information, patient information, patient trends, dosing information, utility options, etc. The main display 4 can e.g., be designed for displaying content comprising complex graphics, such as icons, images, video sequences, etc.

The auxiliary display 5 can be configured for displaying a name of and/or indicator (e.g., an abbreviation and/or a code) for a user, a unit, and/or a location assigned to the respective POCT instrument 1 and/or a user logged into a respective POCT instrument 1. The auxiliary display 5 can e.g., be designed for displaying content comprising letters, numbers, and/or punctuation symbols; the auxiliary display 5 can in particular be configured for displaying ASCII characters. It can be conceivable that the auxiliary display 5 can be designed for displaying simple icons, e.g., a simple battery icon indicating a state of charge of a battery of the POCT instrument 1, e.g., a battery that can be designed for powering the main display 4 and/or the POCT instrument 1.

According to some embodiments, the auxiliary display 5 can be configured for displaying system parameters (e.g., an operation temperature), a network status, a connection status, a status of a consumable (e.g., that a test strip can be inserted into a cavity of the measurement unit 3), a quality control status, an operation status, and/or a battery status.

The auxiliary display 5 can be configured for displaying information such as, for example, in the case the main display 4 is not operational, e.g., during updates, due to software errors, and/or due to hardware errors; the auxiliary display 5 can e.g., be configured for displaying an indication that and/or why the POCT instrument 1 is not operational.

According to some embodiments, the auxiliary display 5 can be configured for only displaying non-medical information, in particular, for only displaying test-result-free information. According to some specific embodiments, the main display 4 can be configured for displaying medical information, in particular, for displaying test-results.

According to some embodiments, the main display 4 and the auxiliary display 5 can each be an electronic visual display, i.e., changing the displayed content can be based on electronic and/or magnetic signals.

According to some embodiments, the main display 4 can be constructed based on a first display technology and the auxiliary display 5 can be constructed based on a second display technology. According to some specific embodiments, the second display technology can consume less power than the first display technology for displaying content, e.g., less than half the power per time unit per area. In an example, the main display 4 can be based on a LCD, LED, OLED, QLED, and/or plasma technology. The auxiliary display 5 can e.g., be based on electrophoretic ink, e.g., as described in U.S. Pat. No. 5,961,804, which is hereby incorporated by reference. For example, the auxiliary display 5 can be based on a display technology as commercially available under the brands E Ink JustTint™, E Ink Prism™, E Ink JustWrite™, E Ink's Spectra™, or E Ink ACeP™ (each as e.g., available on 15 Mar. 2020). According to some specific embodiments, the auxiliary display 5 can be designed for displaying content without consuming power, such as it can e.g., be possible using an electrophoretic ink technology.

According to some embodiments, the main display 4 can be a multicolor display that can be e.g., designed for displaying 255 colors or more (e.g., 32,000 colors or more). The auxiliary display 5 can e.g., be a two-color display and/or a display that can be designed for displaying only a small number of colors (e.g., eight colors or less) and/or a greyscale display.

According to some embodiments, the main display 4 and the auxiliary display 5 can both be pixel-based and the average number of pixels per area-unit of the main display 4 can be larger than that of the auxiliary display 5, e.g., at least four times larger, and in another embodiment, at least ten times larger.

According to some embodiments, the main display 4 can have a larger resolution than the auxiliary display 5. For example, the minimum number of pixels in each dimension of the main display 4 can be at least four times greater and, in another embodiment, at least ten times greater, than the maximum number of pixels in each dimension of the main display 4. A lower resolution can allow for lower production costs and/or lower power consumption.

According to some embodiments, the main display 4 can be larger than the auxiliary display 5, e.g., the visible area of the main display 4 can be at least three times larger, or, in another embodiment, at least six times larger, than that of the auxiliary display 5.

According to some embodiments, the main display 4 can comprise a light source and the auxiliary display 5 may not comprise a light source.

According to some embodiments, the main display 4 can comprise a touch functionality that can allow a user to give input by touching the main display 4. The touch functionality can be provided by a touch sensor, which e.g., can be comprised in an additional layer and/or within the display itself. According to some specific embodiments, the touch functionality can be designed for controlling the POCT instrument 1, the measurement unit 3, and/or the content displayed on the main display 4 and/or the auxiliary display 5. Using a touch functionality can allow for omitting hygienically difficult components (such as e.g., mechanic keys).

According to some embodiments, the auxiliary display 5 may not comprise a touch functionality, e.g., where the content displayed on the auxiliary display 5 can be inputted via a touch functionality of the main display 4 and/or via an external input.

Displays with less color options, with lower pixel density, with smaller visibly area, without a light source, and/or without a touch functionality can have the advantage of being less power-consumptive.

According to some embodiments, the auxiliary display 5 can be designed for displaying a constant content, i.e., displaying the same content over a long period of time. For instance, the auxiliary display 5 can be designed for displaying the same content for multiple weeks, months, or even years without requiring a power supply.

According to some embodiments, the main display 4 respectively a transparent protective layer 7 arranged on top (i.e., on a side on which content can be displayed) of the main display 4 can be arranged in a flush manner with a first side 24 of the housing 2; and/or the auxiliary display 5 respectively a transparent protective layer 7 arranged on top of the auxiliary display 5 can be arranged in a flush manner with a second side 25 of the housing 2. 'Flush' can here e.g., mean with a 1 millimeter or less (e.g., 0.3 millimeter or less) height difference. The first side 24 and the second side 25 can be identical or different. In FIG. 1, a transparent protective layer 7 can be arranged on top of the main display 4 in a flush manner with a side of the housing 2 and the auxiliary display 5 can be arranged in a flush manner with the same side of the housing 2. In the example of FIG. 2, a transparent protective layer 7 can be arranged on top of the main display 4 in a flush manner with a first side 24 of the housing 2 and the auxiliary display 5 can be arranged in a flush manner with a second side 25 of the housing 2 that can be different from the first side 24. The flush construction can e.g., have the advantage of being easier to clean. According to some specific embodiments, the transparent protective layer 7 can be made of a material that can be robust in view of cleaning and/or disinfectant agents, e.g., tempered glass.

According to some embodiments, the housing 2 can be made of a material that can be robust in view of cleaning and/or disinfectant agents, e.g., polycarbonate (PC).

According to some embodiments, the POCT instrument 1 can comprise gaskets made of a thermoplastic elastomer (TPE).

Using robust materials for its components can have the advantage that the POCT instrument 1 can be cleaned/disinfected more often.

In FIG. 3, a first transparent protective layer 74 can be arranged on top of the main display 4 and a second transparent protective layer 75 can be arranged on top of the auxiliary display 5. In FIG. 4, the main display 4 and the auxiliary display 5 can be arranged under a common transparent protective layer 7, which can have the advantage of requiring less transition edges that can be hygienically problematic.

According to some embodiments, the main display 4 and the auxiliary display 5 can be arranged on a same side of the housing 2 and may not be overlapping, such as it can e.g., be seen in FIGS. 1, 3, and 4. According to some specific embodiments, the main display 4 and the auxiliary display 5 can be arranged at a distance from each other, e.g., at a distance of 5 millimeter or more (e.g., 20 millimeters or more). A distance between the displays can have the advantage that the content of the displays can be independently recognizable in an easy manner.

According to some embodiments, the POCT instrument 1 can comprise a switch unit 6 (e.g., as illustrated in FIG. 2), wherein the switch unit 6 can be designed for shutting off the main display 4 but not the auxiliary display 5. 'Shutting off' here can e.g., mean that after shutting off no information may be displayed on the main display 4 anymore, e.g., when the display is switched into a stand-by or sleep mode. The switch unit 6 can e.g., comprise a button such as shown in FIG. 2, a slider, a touch sensor, and/or an electronic switch. The switch unit 6 can e.g., be designed for starting/stopping the POCT instrument's normal operation. The proposed switch unit 6 can have the advantage of allowing a user to start/stop the normal operation of the POCT instrument 1, such as, for example, displaying content on the main display 4 without interfering with displaying content on the auxiliary display 5.

According to some embodiments, the POCT instrument 1 can be configured for shutting off the main display 4 but not the auxiliary display 5 after the POCT instrument 1 has not been used, e.g., received no input, for a certain, e.g., predefined, time period.

The measurement unit 3 can comprise an opening 31, e.g., for inserting biological samples, e.g., test strips with biological material, into the measurement unit 3. The opening 31 can be an opening to a cavity in which a sensor of the measurement unit 3 can be arranged.

As illustrated in FIG. 5, the POCT instrument 1 can comprise electronic components 94 for operating the POCT instrument 1, e.g., for conducting measurements and for displaying results of the measurements on the main display 4. The electronic components 94 can e.g., comprise a control unit 9 (possibly including a processor, a volatile memory, a non-volatile memory, and a bus structure connecting these components) and a power source 8. The control unit 9 can e.g., be controlled by a user via a touch functionality of the main display 4. According to some embodiments, the electric components 94 can be as well designed for operating (e.g. changing the displayed content) of the auxiliary display 5.

According to some embodiments, the main display 4 can comprise a touch sensor 42 for providing touch functionality, such as shown in FIG. 5. The touch sensor 42 can e.g., be comprised in an additional layer and/or within the display itself.

According to some embodiments, the POCT instrument 1 can have a power source that can be powered/charged using a wired power connection.

According to some embodiments, the POCT instrument 1 can comprise a power source 8 that can be charged wirelessly, e.g., by induction. The wirelessly chargeable power source 8 can e.g., be designed for powering a circuitry for operating the main display 4, the auxiliary display 5, and/or the POCT instrument 1. Charging a power source 8 wirelessly can allow for omitting hygienically difficult components (such as e.g., a power socket).

According to some embodiments, the POCT instrument 1 can comprise a wireless communication unit 91, e.g., a Wi-Fi-module, a digital cellular network (e.g., 2G/3G/4G/5G) module, an RFID module, a Bluetooth module, and/or an infrared module. Using wireless communication can allow for omitting hygienically difficult components (such as e.g., a communication socket).

According to some embodiments, the housing 2 can be closed (i.e., without opening), with the possible exception of openings 31 of the measurement unit 3. According to some specific embodiments, the housing can comprise exactly one opening, namely an opening 31 of the measurement unit 3, or no opening. Openings can be hygienically difficult components and limiting the number of openings in the housing 2 can allow for increasing the 'clean-ability' of the POCT instrument 1.

According to some embodiments, the measurement unit 3 can be non-detachable from the POCT instrument 1.

According to some embodiments, the measurement unit 3 can be mechanically integrated into the POCT instrument 1. In an example, the measurement unit 3 can be surrounded by the housing 2 and cannot be removed without dismantling the housing 2, which may comprise overcoming at least one fastening mechanism (e.g., removing a screw). According to some specific embodiments, the measurement unit 3 cannot be removed without damaging the housing 2. Mechanically integrating can increase the functional safety of the POCT instrument 1, e.g., support a precise positioning of an inserted sample relative to the measurement unit 3.

According to some embodiments, all openings of the housing 2 can be designed for inserting biological samples (e.g., carriers carrying the biological samples, e.g., swabs, test strips, and the like) into the POCT instrument 1. According to some specific embodiments, the housing 2 can comprise exactly one opening and that one opening can be designed for inserting biological samples into the POCT instrument 1.

According to some embodiments, the POCT instrument 1 can be fluid-tight. In an example, the POCT instrument 1 can comprise a closed housing 2 made of polycarbonate (PC) and internal gaskets made of thermoplastic elastomers (TPE). The POCT instrument 1 can be designed to communicate and to be charged wirelessly.

According to some embodiments, the POCT instrument 1 can be fluid-tight with the exception of the openings of the measurement unit 3.

Fluid-tightness can improve the hygienic properties of the POCT instrument 1, e.g., increase its 'clean-ability' and/or reduce the risk of cross-contamination.

According to some embodiments, the POCT instrument 1 can comprise a control unit 9 designed for controlling the content displayed on the auxiliary display 5. According to some specific embodiments, the control unit 9 can be further designed for controlling the content displayed on the main display 4. In an example, the control unit 9 can be designed for receiving input via a touch functionality of the main display 4.

According to some embodiments, the measurement unit 3 can be electronically integrated into the POCT instrument 1. According to some specific embodiments, the measurement unit 3 can be electronically connected to a control unit 9 designed for controlling the content displayed on the main display 4 via an electronic connection that cannot be separated without damaging the electronic connection. In an example, the measurement unit 3 and the control unit 9 can be welded to a same circuit board. According to some specific embodiments, the electronic connection can comprise one or more plug connections, each of which cannot be opened without damaging the plug connection. Electronically integrating can increase the functional safety of the POCT instrument 1.

Figure 6:
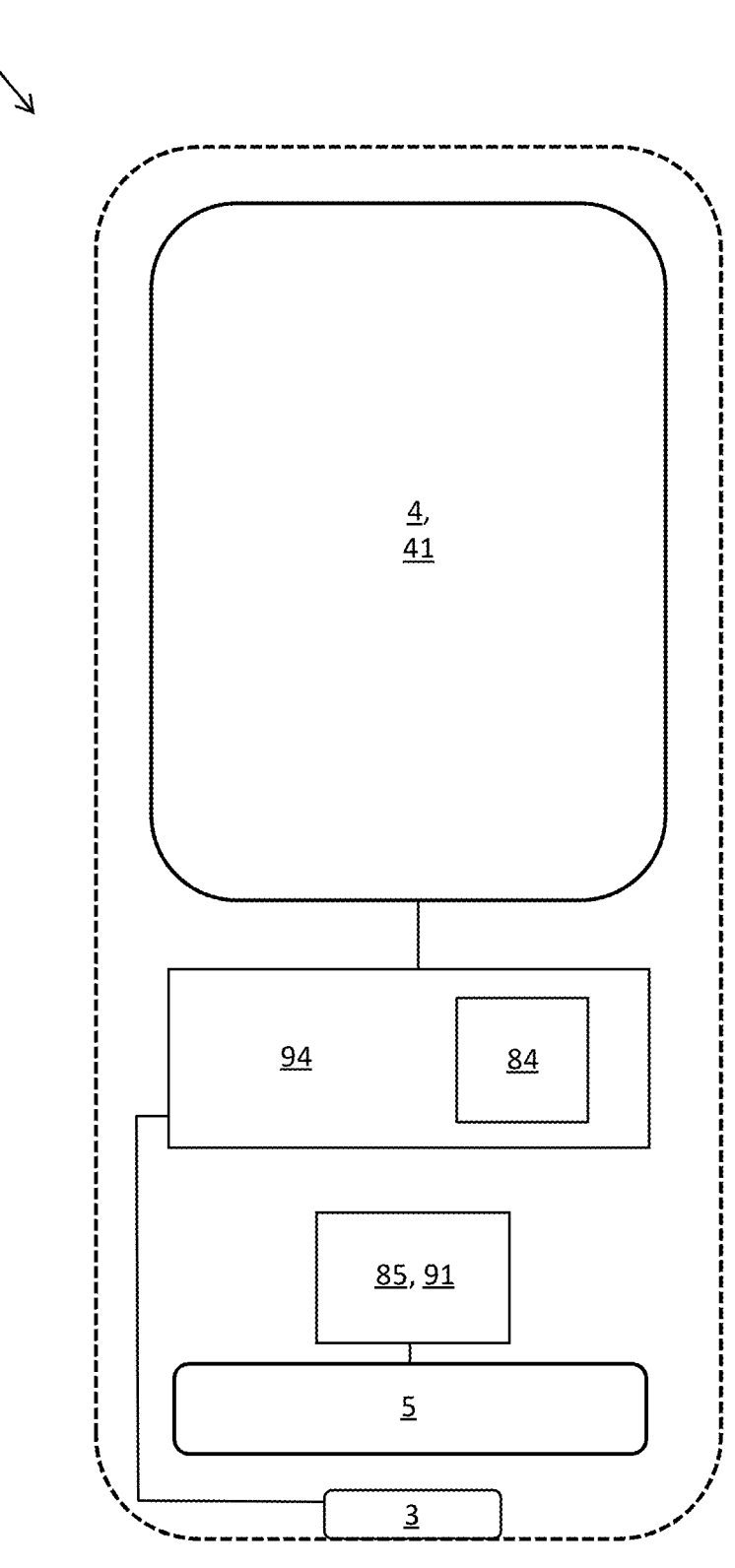
FIG. 6 illustrates a schematic of another POCT instrument's electronics according to an embodiment of the present disclosure.

According to some embodiments, the POCT instrument 1 can comprises a first power source 84 and a second power source 85, as shown in FIG. 6, wherein the POCT instrument 1 can be designed such that the main display 4 can be supplied by the first power source 84 and the auxiliary display 5 can be supplied by the second power source 85. According to some specific embodiments, the first power source 84 can comprise a battery and a coil for inductively charging the battery. In addition, or alternatively, the second power source 85 can comprise a coil for inductively powering the auxiliary display 5, e.g., for changing the content displayed thereon.

In the example shown in FIG. 6, the auxiliary display 5 may not require power for displaying content, but may require power for changing displayed content; and the command for changing the displayed information together with the necessary energy for the changing can be induced from an external source via a coil of the second power source 85, which thereby can act as a part of a wireless communication unit 91.

As shown in example of FIG. 6, the circuitry of the auxiliary display 5 can be independent of the circuitry of the main display 4, which can allow displaying information on the auxiliary display 5 in the case where the circuitry of the main display 4 is not operational, e.g., due to hardware errors.

According to some embodiments, the main display 4 can comprise a light source 41. According to some specific embodiments, the auxiliary display 5 may not comprise a light source. A display without a light source can be less power-consumptive and possibly does not require power for displaying content.

Figure 7:
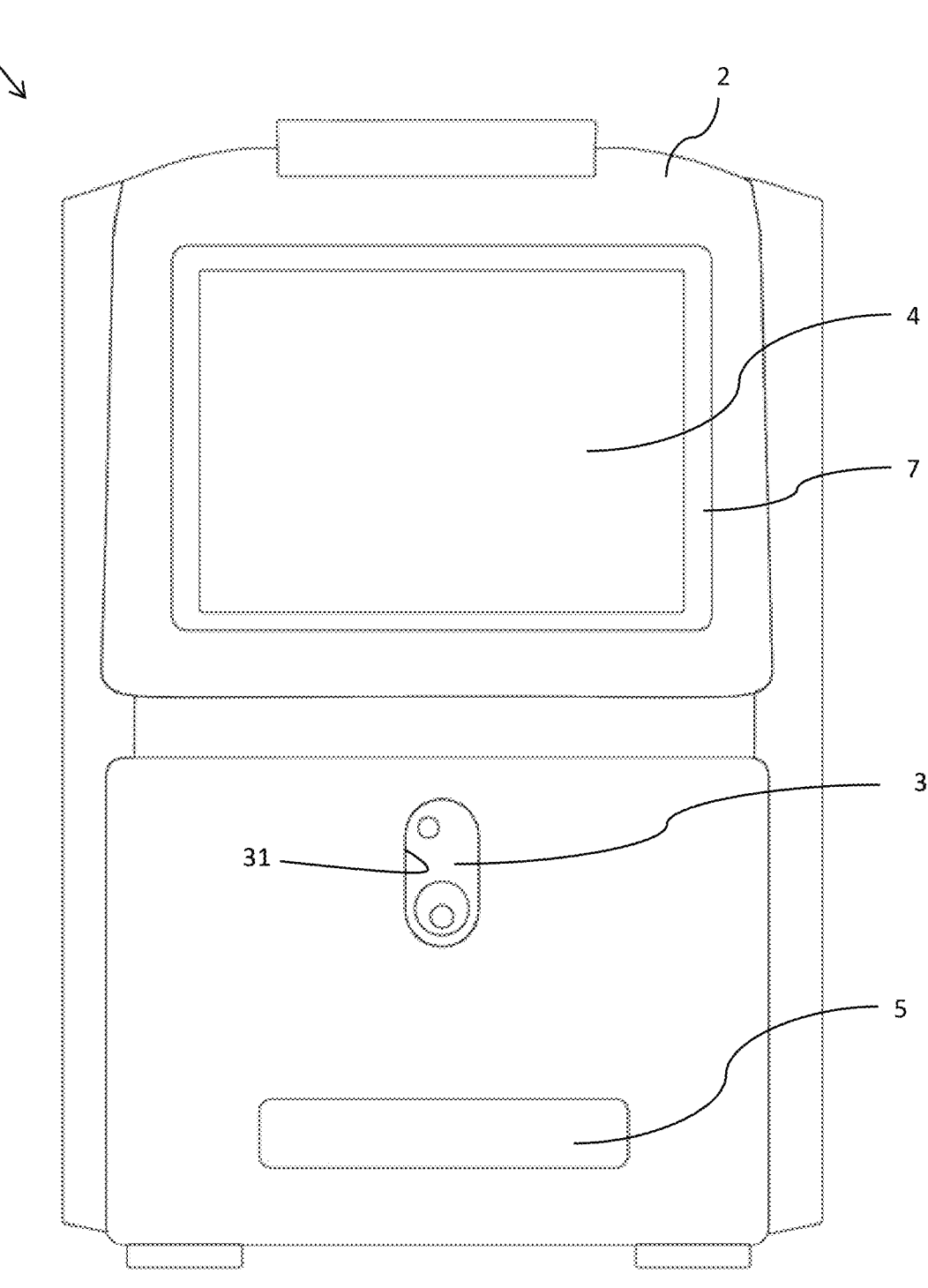
FIG. 7 illustrates a front view of a POCT instrument in form of a benchtop device according to an embodiment of the present disclosure.

FIG. 7 illustrates an example of a proposed POCT instrument 1 in form of a benchtop device.

Figure 8:
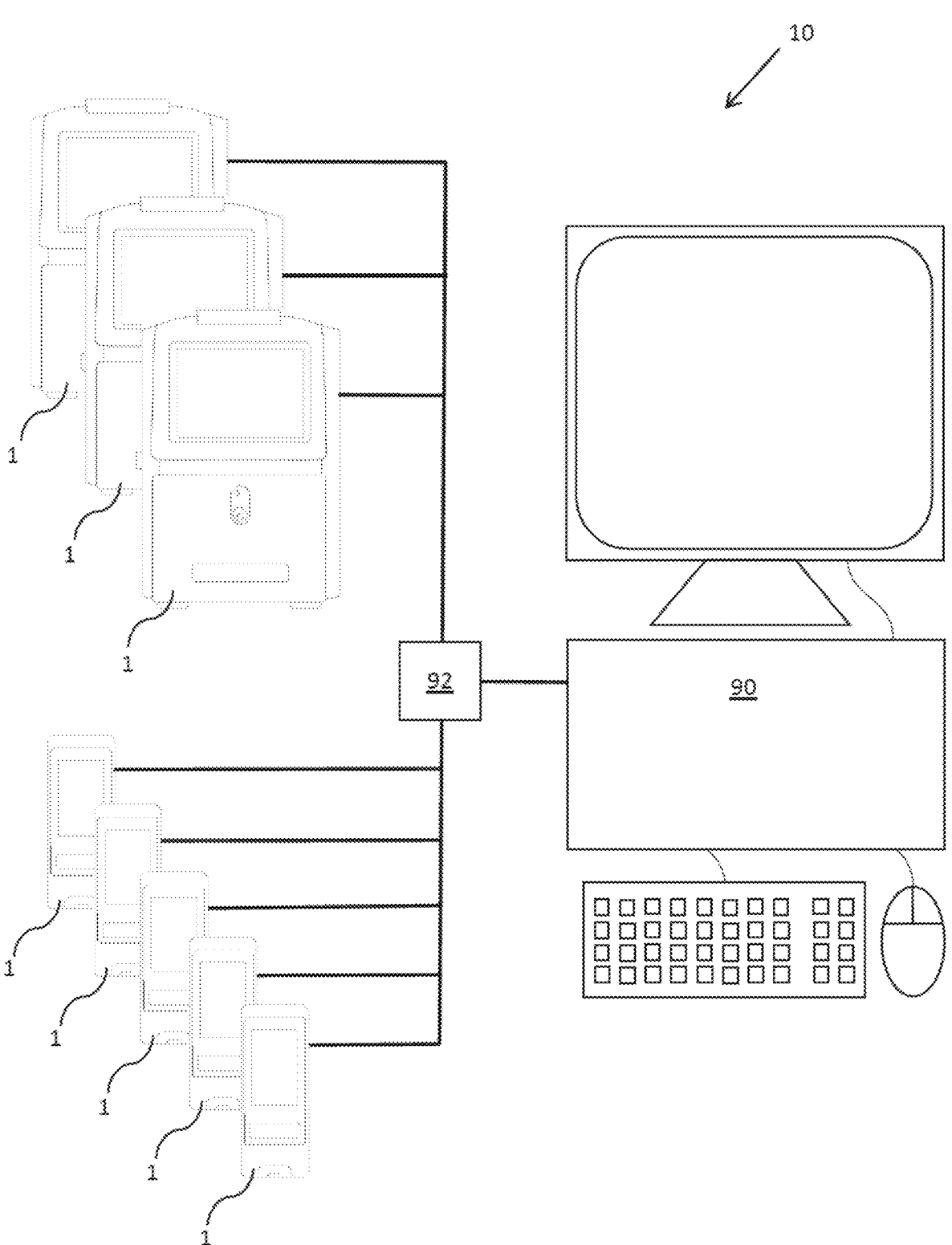
FIG. 8 illustrates a POCT system according to an embodiment of the present disclosure.

FIG. 8 illustrates a POCT system 10 comprising a plurality of POCT instruments 1, each of which e.g., being of one of the types shown in FIGS. 1-4, and 7. Such a POCT system 10 can comprise dozens, hundreds, or even thousands of POCT instruments 1. The POCT system 10 can further comprise a system control unit 90 that can be designed for changing the content displayed on the auxiliary display 5 of at least one, e.g., any one, of the POCT instruments 1.

As illustrated in FIG. 8, the POCT system 10 can comprise a communication network 92 via which the POCT instruments 1 can be connectable to the system control unit 90. The communication network 92 can comprise wireless and/or wired connections. According to some specific embodiments, the POCT system 10 can be designed so that the system control unit 90 can transmit instructions concerning content to be displayed on an auxiliary display 5 via the communication network 92 to a POCT instrument 1 comprising that auxiliary display 5. In an example, the system control unit 90 can transmit to a POCT instrument 1 that this particular POCT instrument 1 can be assigned to a new unit within a hospital, and the POCT instrument 1. e.g., a control unit thereof, can instruct the auxiliary display 5 to henceforth display symbols indicating the new unit.

According to some specific embodiments, some POCT instruments 1 can be benchtop devices that can be connected to the system control unit 90 via wired connections and some POCT instruments 1 can be handheld devices that can be connected to the system control unit 90 via wireless connections.

Figure 9:
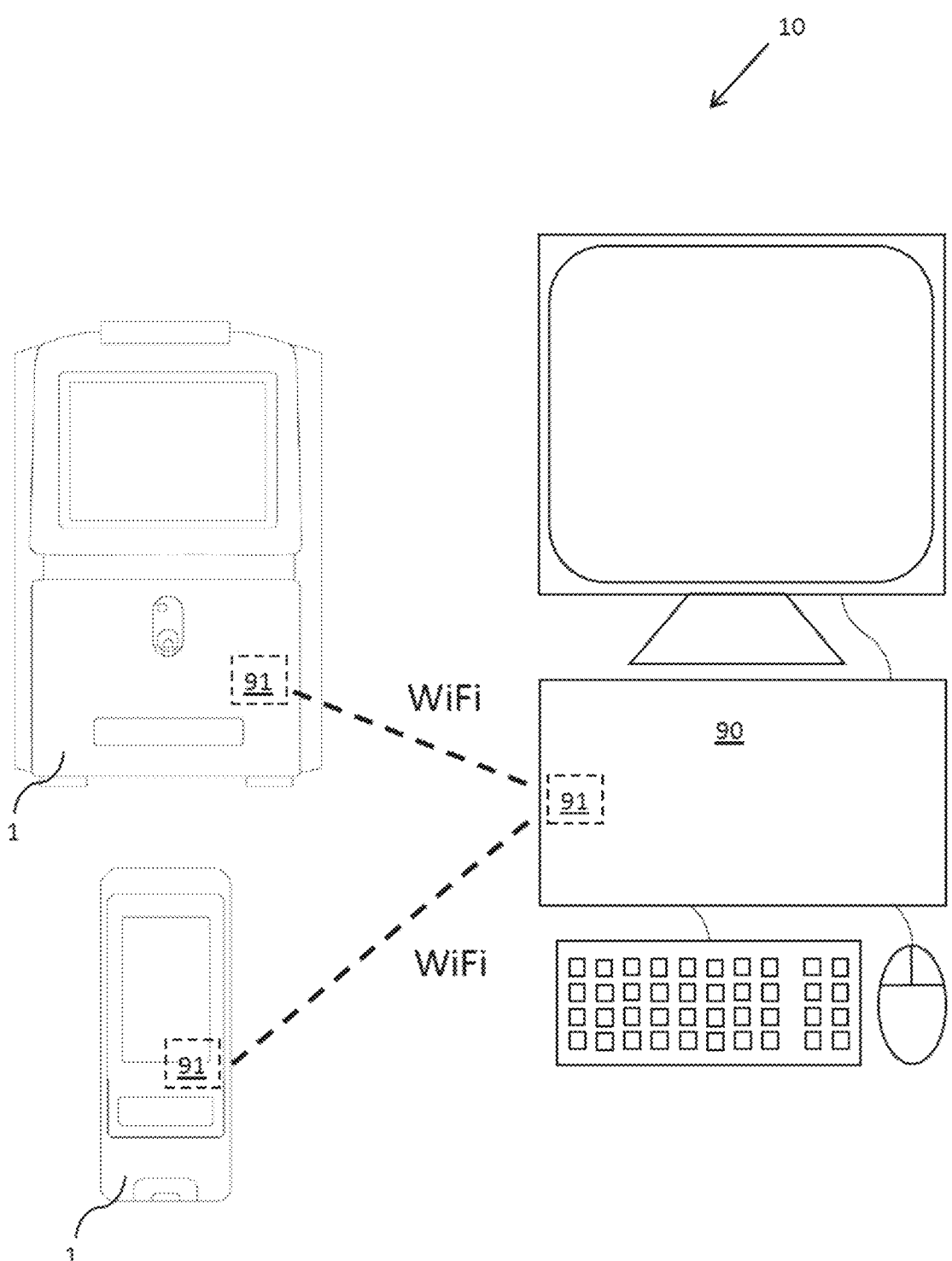
FIG. 9 illustrates a POCT system using Wi-Fi connections according to an embodiment of the present disclosure.
Figure 10:
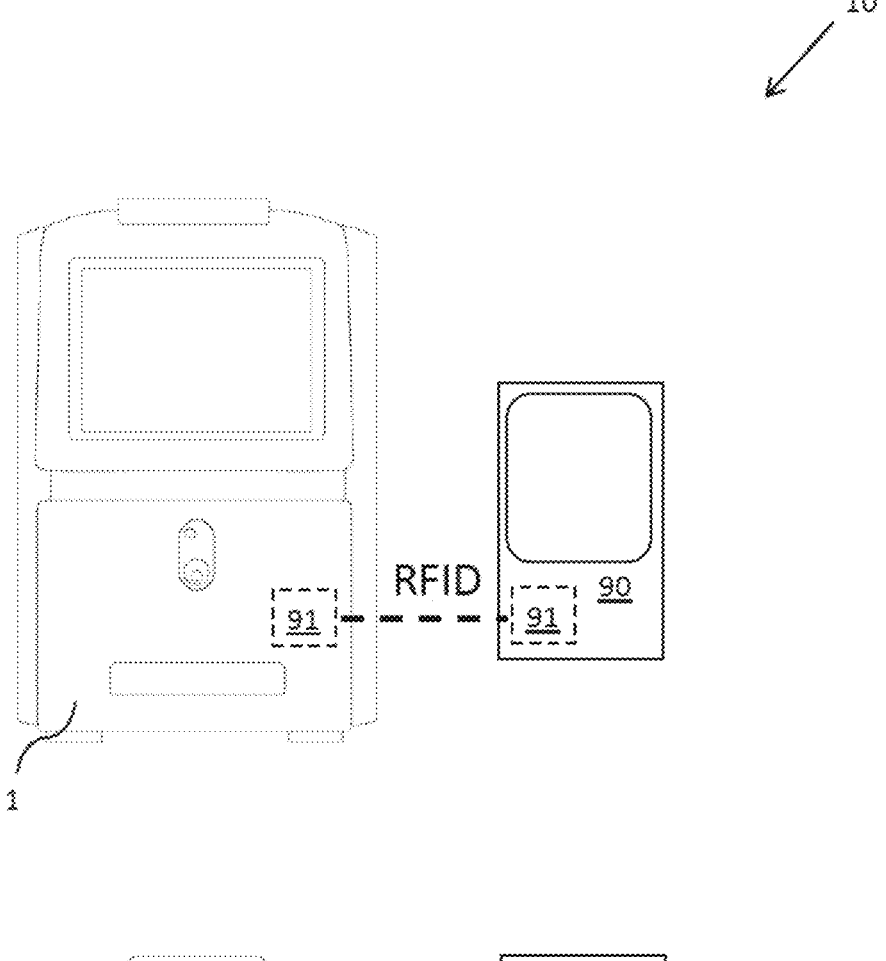
FIG. 10 illustrates a POCT system using RFID connections according to an embodiment of the present disclosure.

According to some embodiments, the system control unit 90 and the POCT instruments 1 can each comprise a wireless communication unit 91, e.g., as part of a communication network. The wireless communication units 91 can allow changing the content displayed on an auxiliary display 5 of a POCT instrument 1 using a wireless signal. Such a wireless communication unit 91 can e.g., comprise a Wi-Fi-module, a digital cellular network module, a RFID module, a Bluetooth module, and/or an infrared module. As illustrated in FIG. 9, the system control unit 90 can comprise a centralized unit (e.g., a server and/or a data management system), which according to some specific embodiments can connect to a POCT instruments 1 from afar, e.g., using a Wi-Fi network. As illustrated in FIG. 10, the system control unit 90 can comprise a portable/handheld device, which according to some specific embodiments can connect to a nearby POCT instrument 1, e.g., using an RFID connection. The portable/handheld device can be designed for inductively transmitting power to circuitry that can be connected to the auxiliary display 5, e.g., power needed for changing the content displayed on the auxiliary display 5.

As can e.g., be seen in FIGS. 8 to 10, the system control unit 90 can be external to the POCT instrument 1 and, in particular, not comprised in the housing 2 of the POCT instrument 1. The POCT instrument 1 can be designed for changing content displayed on the auxiliary display 5 according to instructions inputted via an external input device. The instructions can be direct, e.g., comprise an exact string to be displayed, and/or indirect, e.g., comprise a numerical code that can indicate the name of the ward to be displayed. The external input device can e.g., be a keyboard of a system control unit 90, e.g., as shown in FIG. 9, or a touchscreen of a portable/handheld device of the system control unit 90, e.g., as shown in FIG. 10. According to some specific embodiments, the POCT system 10 can be designed for wirelessly transmitting instructions that were inputted via the external input device to the POCT instrument 1, e.g., via a shared wireless communication unit 91 of the POCT instrument 1 that can be connected to the auxiliary display 5 and to the main display 4 and/or via a dedicated wireless communication unit 91 of the POCT instrument 1 that can be connected to the auxiliary display 5 but not to the main display 4.

According to some embodiments, the POCT system 10 can be designed for automatically adjusting the content displayed on the auxiliary display 5 of a POCT instrument 1 to data stored in the system control unit 90. In an example, the system control 90 unit can comprise a database; the database can comprise a field for each of the POCT instruments 1 (the field e.g., comprising the name of a user allocated to the respective POCT instrument 1); the system control unit 90 can be designed for automatically transmitting-if the content in such a field is changed—the new content of this field to the respective POCT instrument 1; and the POCT instrument 1 can be designed for displaying the transmitted new content on the auxiliary display 5. Of course, a single field of the database can also be used for the content displayed on the auxiliary displays 5 of multiple POCT instruments 1, e.g., all POCT instruments 1 of a same ward. Automatically keeping the content displayed on the auxiliary display 5 adjusted to data stored in the system control unit 90 can allow simplifying the administration of the POCT system 10.

According to some embodiments, the POCT system 10 can be designed for automatically adjusting the content displayed on the auxiliary display 5 of a POCT instrument 1 to data stored in the system control unit 90 in the sense that the content displayed on the auxiliary display 5 of the POCT instrument 1 can be based on data stored in the system control unit 90 (e.g., in a pre-determined manner) and, if this stored data is adjusted in the system control unit 90, the adjusted data can be automatically transmitted to the POCT instrument 1 and a new content that can be based on the adjusted data (e.g., in the same pre-determined manner) can thereafter be displayed on the auxiliary display 5. In an example, a hospital can encode the names of its wards in a database of the system control unit 90 using codes and the POCT instrument 1 can be designed for translating the codes to the names of the wards (e.g., by using a respective a translation table); and if the respective code in the system control unit 90 is altered to a new code representing a new ward, automatically, the new code can be transmitted to the POCT instrument 1, translated to the name of the new ward by the POCT instrument 1 using the translation table, and the name of new ward can then be displayed on the auxiliary display 5.

According to some specific embodiments, the POCT system 10 can be designed for automatically adjusting the content displayed on the auxiliary display 5 of a POCT instrument 1 to data stored in the system control unit 90 in the sense that content displayed on the auxiliary display 5 of the POCT instrument 1 can depend on a data string that is stored in the system control unit 90 and, if this data string is adjusted (e.g., the sequence of characters of the data string is altered) in the system control unit 90, the adjusted data string can automatically be transmitted to the POCT instrument 1 and content depending on the adjusted data string can thereafter be displayed on the auxiliary display 5. The content can e.g., be the (adjusted) data string itself and/or derived therefrom in a pre-defined manner, e.g., the name of a staff member depending on a code.

According to some embodiments, the POCT system 10 can comprise a docking station. According to some specific embodiments, the docking station can be designed for charging a POCT instrument 1 such as, for example, a power source 8 of a handheld POCT instrument 1. The docking station can be designed for wirelessly charging the POCT instrument 1, e.g., using induction. In addition, or alternatively, the docking station can be designed for charging the POCT instrument 1 using a wired connection, e.g., where the docking station and the POCT instrument 1 can each comprise respective connectors for transferring power via the connected connectors. The docking station can be designed for receiving the POCT instrument 1 in a pre-defined manner such that the respective connectors can be connected when the POCT instrument 1 is received in the docking station in that pre-defined manner, e.g., where parts of the docking station can be designed as the negative to parts of the exterior shape of the POCT instrument 1.

According to some embodiments, the docking station can be designed for exchanging data with a POCT instrument 1 such as, for example, with a communication unit 91 of the POCT instrument 1. The docking station can be a part of the communication network 92 and/or connected to a system control unit 90. According to some specific embodiments, the docking station can be designed for wireless communication with the POCT instrument 1. The docking station can comprise a communication module, e.g., a Wi-Fi-module, a digital cellular network (e.g., 2G/3G/4G/5G) module, an RFID module, a Bluetooth module, and/or an infrared module such as, for example, a communication module that can correspond to a respective module of the communication unit 91 of the POCT instrument 1. In addition, or alternatively, the docking station can be designed for wired communication with the POCT instrument 1, e.g., where the docking station and the POCT instrument 1 can each comprise respective connectors for transferring data via the connected connectors. The docking station can be designed for receiving the POCT instrument 1 in a pre-defined manner such that the respective connectors can be connected when the POCT instrument 1 is received in the docking station in that pre-defined manner, e.g., where parts of the docking station can be designed as the negative to parts of the exterior shape of the POCT instrument. The connectors for transferring data can further be designed for transferring power, e.g., where the connectors can adhere to the USB standard.

According to some embodiments, the POCT system 10 can comprise a plurality of handheld POCT instruments 1 and a plurality of docking stations.

According to some embodiments, the POCT instrument 1 can comprise an authorization module for selectively authorizing a user of the POCT instrument 1 for using a certain functionality of the POCT instrument 1, e.g., for using a measurement unit 3 and/or a particular test routine. In an example, the authorization module can be designed for blocking a user from performing a certain test if the necessary certificates for proving the user's familiarity with those particular tests are not available. The authorization unit can e.g., be realized as a software executable on the control unit 9. The POCT instrument 1 can comprise an identification module for identifying a user. The identification module can comprise hardware, e.g., a reading unit for reading identification (e.g., a barcode and/or RFID reader) or an input unit, e.g., a touch sensor 42 of the main display 4. The authorization module can be designed for selectively authorizing a user using an identification of the user provided by the identification unit. The authorization module can allow for controlling and/or administrating regulatory requirements concerning the training of the users of for POCT instruments.

According to some embodiments, the authorization module can comprise a list of users and functionalities of the POCT instrument 1 and the list can specify which of the users can be authorized for using which functionalities. The POCT system 10 can be designed for sending and/or updated the list from the system control unit 90 to the POCT instrument 1.

According to some embodiments, the POCT system 10 can be designed so that the authorization module can communicate with the system control unit 90 and can request information from the system control unit 90 as to which functionalities a specific user scan be allowed to use, e.g., by sending data on this specific user (e.g., data acquired using the identification module) to the system control unit 90. According to an example, the system control unit 90 can comprise a respective authorization list and can be designed for returning to the POCT instrument 1 a set of functionalities that this specific user can be allowed to use based on the authorization list.

According to some embodiments, the POCT instrument 1 can be designed for transmitting information (e.g., information concerning test results, information concerning quality control results, information concerning trainings conducted on the POCT instrument 1) to the system control unit 90. The transmitted information can allow determining a training level of a user and/or a quality control status of the POCT instrument 1, can allow supporting audits, and/or can allow the further use of test results, e.g., in a hospital information system and/or by a medical practitioner.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A point of care testing (POCT) instrument for analyzing biological samples, the POCT instrument comprising:
a housing;
a measurement unit designed for collecting data indicative of at least one biological parameter of a biological sample;
a main display; and
an auxiliary display wherein the main display, the auxiliary display, and the measurement unit are each integrated into the same housing.

2. The POCT instrument of claim 1, wherein content displayed on each of the main display and the auxiliary display is visible from outside the housing.

3. The POCT instrument of claim 1, wherein the main display is arranged on a first side of the housing and the auxiliary display is arranged on a second side of the housing.

4. The POCT instrument of claim 1, wherein a circuitry of the auxiliary display is independent of a circuitry of the main display.

5. The POCT instrument of claim 1, further comprises,
a first power source; and
a second power source, wherein the main display is supplied by the first power source and the auxiliary display is supplied by the second power source.

6. The POCT instrument of claim 1, wherein the average number of pixels per area-unit of the main display is at least four times larger than that of the auxiliary display.

7. The POCT instrument of claim 1, wherein the housing comprises no openings or only openings for the measurement unit.

8. The POCT instrument of claim 1, wherein the main display comprises a touch functionality and the auxiliary display does not comprise a touch functionality.

9. The POCT instrument of claim 1, wherein the main display and the auxiliary display are arranged under a common transparent protective layer.

10. The POCT instrument of claim 1, further comprises,
a switch unit designed for shutting off the main display but not the auxiliary display.

11. The POCT instrument of claim 1, wherein the main display is constructed based on a first display technology and the auxiliary display is constructed based on a second display technology.

12. The POCT instrument of claim 11, wherein the second display technology consumes less than half power per time unit per area than the first display technology.

13. The POCT instrument of claim 1, wherein the auxiliary display is designed for displaying content without power consumption.

14. The POCT instrument of claim 1, wherein the auxiliary display requires power for changing displayed content and wherein the POCT instrument is designed so that the command for changing content displayed on the auxiliary display and the necessary energy for this changing can be induced from an external source.

15. The POCT instrument of claim 1, wherein the auxiliary display is designed for displaying a constant content.

16. The POCT instrument of claim 1, wherein the visible area of the main display is at least three times larger than that of the auxiliary display.

17. The POCT instrument of claim 1, wherein the POCT instrument is designed for changing content displayed on the auxiliary display according to instructions inputted via an external input device.

18. The POCT instrument of claim 1, wherein the main display and/or a transparent protective layer arranged on top of the main display is arranged in a flush manner with a first side of the housing and the auxiliary display and/or a transparent protective layer arranged on top of the auxiliary display is arranged in a flush manner with a second side of the housing.

19. The POCT instrument of claim 1, wherein the main display and the auxiliary display are arranged on a same side of the housing and are not overlapping.

20. The POCT instrument of claim 1, further comprises, an authorization module for selectively authorizing a user of the POCT instrument to use certain functionality of the POCT instrument.

21. A POCT system, the POCT system comprising:

a plurality of POCT instruments according to claim 1; and a system control unit, wherein the system control unit is designed for changing the content displayed on the auxiliary displays of the POCT instruments wherein the auxiliary display of each POCT instrument is configured to display a name or an indicator of a user, a unit or a location assigned to the POCT instrument.

22. The POCT system of claim 21, wherein the POCT system is designed for automatically adjusting the content displayed on the auxiliary display of a POCT instrument of the plurality of POCT instruments to data stored in the system control unit.

23. The POCT system of claim 22, wherein the POCT system is designed such that content displayed on the auxiliary display of a POCT instrument of the plurality of POCT instruments is based on data stored in the system control unit and, if this stored data is adjusted in the system control unit, the adjusted data is automatically transmitted to the POCT instrument and content based on the adjusted data is displayed on the auxiliary display.

24. The POCT system of one of claim 21, wherein the POCT instrument is designed for transmitting information concerning test results to the system control unit.

25. The POCT instrument of claim 1, wherein the auxiliary display is configured to display a name or an indicator of a user, a unit or a location assigned to the POCT instrument.

26. The POCT instrument of claim 1, wherein the POCT instrument has a substantially flat cuboid shape and the main display is arranged on a large side of the POCT instrument and the auxiliary display is arranged on a small side of the POCT instrument.

\* \* \* \* \*